US00PP37384P2

(12) United States Plant Patent
Carrella

(10) Patent No.: US PP37,384 P2
(45) Date of Patent: Apr. 28, 2026

(54) ***CALIBRACHOA* PLANT NAMED 'KLECA24A64'**

(50) Latin Name: *Calibrachoa hybrida*
Varietal Denomination: KLECA24A64

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/252,697

(22) Filed: Jun. 27, 2025

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Calibrachoa* plant particularly distinguished by having pink flowers with a red-purple center; and a short-lived subshrub form with a trailing habit, is disclosed.

1 Drawing Sheet

Genus and species: *Calibrachoa hybrida.*
Variety denomination: 'KLECA24A64'.

BACKGROUND OF THE NEW PLANT

The present invention comprises a new and distinct variety of *Calibrachoa*, botanically known as *Calibrachoa hybrida*, and hereinafter referred to by the variety name 'KLECA24A64'. 'KLECA24A64' originated from an open pollination between the proprietary female *Calibrachoa* variety 'CA-2020-0024' (unpatented) and an unknown male *Calibrachoa* plant.

In July 2020, seeds from the open pollination were collected from the female *Calibrachoa* plant 'CA-2020-0024' in Stuttgart, Germany. The seeds were sown and plants were grown for evaluation. A plant line was selected in the spring of 2021 in Stuttgart, Germany and subsequently named 'KLECA24A64'. In the spring of 2021 in Stuttgart, Germany, 'KLECA24A64' was first vegetatively propagated by cuttings. 'KLECA24A64' was found to reproduce true to type in successive generations of asexual propagation via cuttings.

SUMMARY

The following are the most outstanding and distinguishing characteristics of this new variety when grown under normal horticultural practices in Stuttgart, Germany.

1. Pink flowers with a red-purple center; and
2. A short-lived subshrub form with a trailing habit.

DESCRIPTION OF THE PHOTOGRAPH

This new *Calibrachoa* plant is illustrated by the accompanying photograph which shows a close-up of the whole plant. The photograph is of a 11-week-old-plant grown in a greenhouse in Stuttgart, Germany in May 2024. The colors shown are as true as can be reasonably obtained by conventional photographic procedures.

DESCRIPTION OF THE NEW VARIETY

The following detailed descriptions set forth the distinctive characteristics of 'KLECA24A64'. The data which define these characteristics were collected from asexual reproductions carried out in Latina, Italy. Data was collected on 14-week old plants after transplant in Latina, Italy. Color references are to The R.H.S. Colour Chart of The Royal Horticultural Society of London (R.H.S.), 5$^{th}$ edition (2007).

Classification:
- *Family.*—Solanaceae.
- *Species.*—*Calibrachoa hybrida.*
- *Common name.*—*Calibrachoa.*

Parentage:
- *Female.*—'CA-2020-0024' (unpatented).
- *Male.*—Unknown.

Plant description:
- *Life cycle.*—Annual.
- *Form.*—Short-lived subshrub.
- *Habit.*—Trailing.
- *Height (from soil line to top of foliage).*—5.5 cm.
- *Spread.*—57.1 cm.

Propagation:
- *Type cuttings.*—Tip cuttings.
- *Time to produce a rooted cutting.*—3 weeks.
- *Flowering.*—8 weeks from potting.

Stems:
- *Stem color.*—RHS 144B.
- *Pubescence.*—Present.
- *Pubescence color.*—RHS 155A.
- *Stem diameter.*—0.1 cm.
- *Stem length.*—From soil line to first node: 0.5 cm. Total length: 33.4 cm.
- *Internode length.*—1.8 cm.

Leaves:
- *Arrangement.*—Alternate.

*Shape*.—Cuneate.
*Apex*.—Obtuse.
*Base*.—Acute.
*Margin*.—Ciliate.
*Surface*.—Pubescent.
*Pubescence color*.—RHS 155A.
*Venation color*.—Upper surface: RHS 138B. Lower surface: RHS 138B.
*Length*.—2.6 cm (mature leaves, average size).
*Width*.—1.3 cm (mature leaves, average size).
*Color*.—Upper surface: RHS 137B. Lower surface: RHS 138B. Fragrance: Absent.

Flowers:
*Flowering habit*.—Single flower.
*Flower type*.—Single.
*Number of flowers produced per season*.—250 flowers or more depending on cultivation.
*Duration of flowers*.—7 to 12 days.
*Corolla*.—Smooth.
*Shape*.—Funnel form.
*Fragrance*.—Absent.

Flower buds:
*Number of buds produced per season*.—250 buds or more depending on cultivation.
*Surface*.—Pubescent.
*Length*.—2.5 cm.
*Diameter*.—0.5 cm.
*Shape*.—Irregular to oblong.
*Color*.—RHS 77A (middle part of buds) and RHS 75A (top buds), RHS 150D (base buds).

Pedicels:
*Typical and observed pedicel length*.—1.5 cm.
*Diameter*.—Less than 0.1 cm.
*Texture*.—Pubescent.

Peduncle:
*Length*.—1.5 cm.
*Diameter*.—Less than 0.1 cm.
*Color*.—RHS 144B.
*Texture*.—Pubescent.
*Anthocyanin color*.—RHS 77A.

Flower description:
*Flower depth*.—2.4 cm.
*Flower tube length*.—1.5 cm.
*Flower tube diameter*.—0.4 cm.
*Flower throat diameter*.—0.9 cm.
*Flower diameter*.—4.9 cm average size measured.
*Pedicel color*.—RHS 144B.

Sepals:
*Number of sepals per flower*.—Five sepals.
*Shape*.—Ovate.
*Apex*.—Narrow acute.
*Margin*.—Denticulate.
*Length*.—1.2 cm.
*Diameter*.—0.4 cm.
*Texture (both surfaces)*.—Pubescent.
*Sepal color*.—Upper surface: RHS 143A. Lower surface: RHS 144C.

Petals:
*Number of petals per flower*.—Five.
*Shape*.—Rounded.
*Apex*.—Obtuse.
*Margin*.—Entire.
*Base*.—Fused into a tube.
*Texture*.—Smooth.
*Pubescence*.—Absent.
*Lobe length*.—2.1 cm.
*Lobe width*.—2.1 cm.
*Color*.—Lobe color: Upper surface: RHS 69B main color, RHS N74A center pattern color, RHS N74A veins. Lower surface: RHS 69B main color, RHS N74A veins. Corolla tube color: Inner: RHS 12D. Outer: RHS 4C.
*Fragrance*.—Absent.

Reproductive organs:
*Stamen number*.—5.
*Stamen color*.—Anther color: RHS 13B. Filament color: RHS 1C. Pollen color: RHS 12B.
*Ovary*.—Placenta arrangement: Ovate. Pistil number: 1. Pistil length: 0.7 cm. Stigma color: RHS 145B. Style length: 0.6 cm. Style color: RHS 145B. Pollen amount: Moderate.

Fruit/seed set: None observed.

Disease/insect resistance: No pests and disease were observed.

COMPARISON WITH FEMALE PARENT AND KNOWN VARIETY

'KLECA24A64' is distinguished from its female parent as described in Table 1:

TABLE 1

Comparison with Female Parent

| Trait | Variety 'KLECA24A64' | Female parent |
|---|---|---|
| Color pattern | Pink flowers with a red-purple center | Red center with yellow stripes |

'KLECA24A64' is most similar to the *Calibrachoa* plant named 'KLECA24A17' (unpatented). Differences between the two varieties are described in Table 2:

TABLE 2

Comparison with Similar Variety

| Trait | Variety 'KLECA24A64' | Commercial line 'KLECA24A17' |
|---|---|---|
| Main flower color | Pink flowers with a red-purple center | Light blue with dark blue center |

I claim:

1. A new and distinct cultivar of *Calibrachoa* plant named 'KLECA24A64' as shown and described herein.

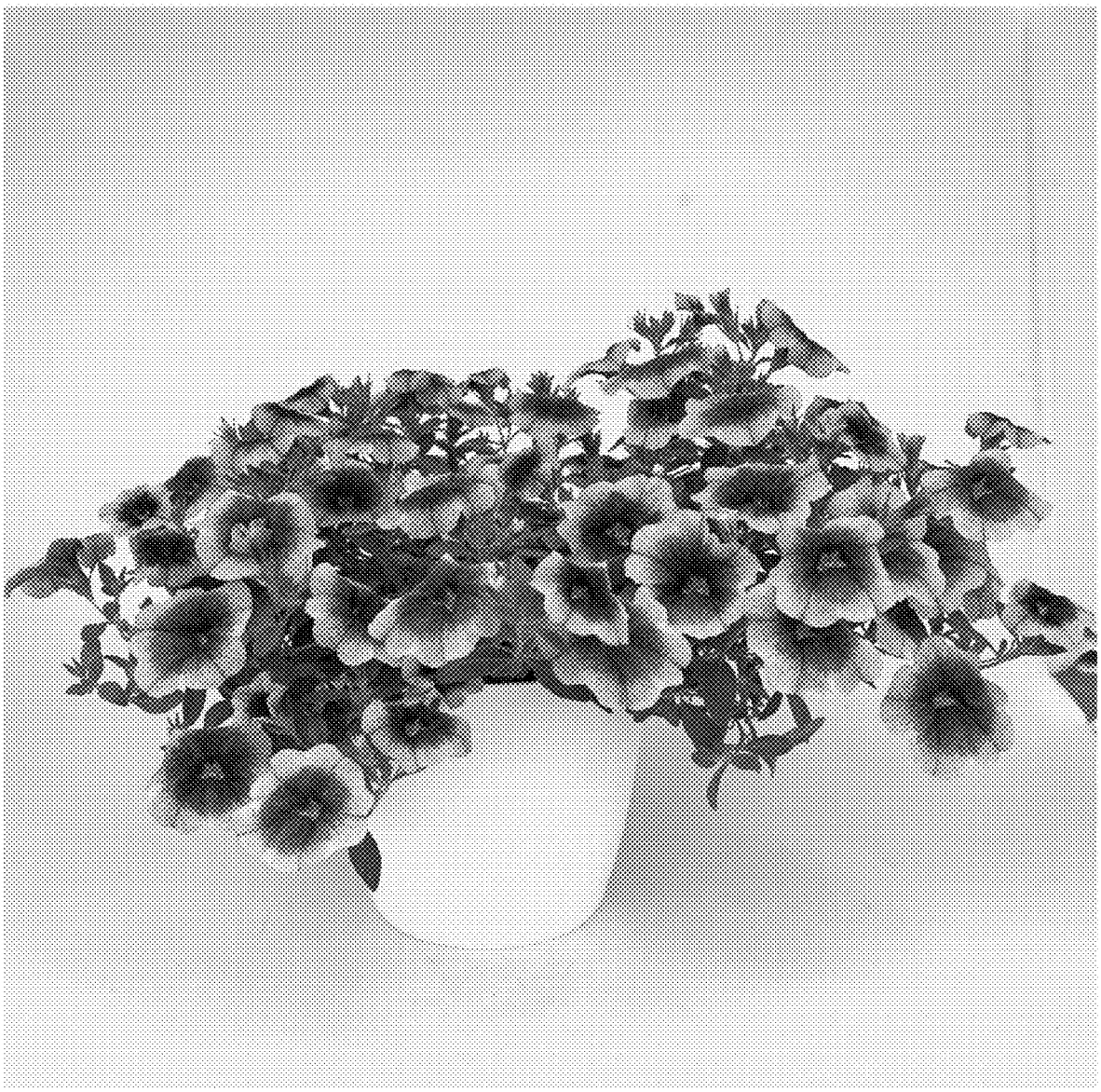

* * * * *